(12) United States Patent
Cheon et al.

(10) Patent No.: US 11,484,330 B2
(45) Date of Patent: Nov. 1, 2022

(54) BASKET ACTUATOR AND SURGICAL DEVICE INCLUDING THE SAME

(71) Applicant: EASYENDO SURGICAL, INC., Daejeon (KR)

(72) Inventors: Byung Sik Cheon, Daejeon (KR); Dong Soo Kwon, Daejeon (KR)

(73) Assignee: ROEN Surgical, Inc., Daejeon (KR)

( * ) Notice: Subject to any disclaimer, the term of this patent is extended or adjusted under 35 U.S.C. 154(b) by 75 days.

(21) Appl. No.: 17/099,799

(22) Filed: Nov. 17, 2020

(65) Prior Publication Data
US 2022/0054152 A1 Feb. 24, 2022

(30) Foreign Application Priority Data

Aug. 24, 2020 (KR) .................. 10-2020-0106460

(51) Int. Cl.
*A61B 17/221* (2006.01)
*A61B 17/22* (2006.01)

(52) U.S. Cl.
CPC .... *A61B 17/221* (2013.01); *A61B 2017/2212* (2013.01); *A61B 2017/22038* (2013.01)

(58) Field of Classification Search
CPC . A61B 17/221; A61B 17/29; A61B 17/32056; A61B 2017/22038; A61B 2017/22084; A61B 2017/2212; A61B 2017/2215; A61B 2017/2017; A61B 2017/2903; A61B 2017/2912; A61B 2017/2915; A61B 2017/2916; A61B 2017/2917; A61B 1/0008; A61B 1/00085; A61B 1/00087; A61F 2/95; A61F 2002/9528; A61F 2002/9534

USPC .................................................. 606/127, 200
See application file for complete search history.

(56) References Cited

U.S. PATENT DOCUMENTS

| | | | |
|---|---|---|---|
| 5,788,710 A * | 8/1998 | Bates | A61B 17/221 606/127 |
| 6,258,101 B1 | 7/2001 | Blake, III | |
| 6,348,056 B1 * | 2/2002 | Bates | A61B 17/221 606/113 |
| 2002/0010485 A1 * | 1/2002 | Griego | A61B 17/32056 606/167 |

(Continued)

FOREIGN PATENT DOCUMENTS

| | | |
|---|---|---|
| JP | 2016101315 | 6/2016 |
| KR | 20120086233 | 8/2012 |

(Continued)

*Primary Examiner* — Kathleen S Holwerda
*Assistant Examiner* — Kankindi Rwego
(74) *Attorney, Agent, or Firm* — JCIPRNET

(57) ABSTRACT

A basket actuator includes a base including a base body and a base guide installed in the base body, a slider including a slider body configured to slide along the base guide, and a first slider arm and a second slider arm formed to protrude from the slider body and facing each other, a roller including a roller body rotatably disposed between the first slider arm and the second slider arm and a plurality of roller blades formed to protrude outwardly from the roller body, a wire guide connected to a front end portion of the base body, a wire disposed inside the wire guide and having a first end fixed to the roller, and a basket connected to a second end of the wire. The second slider arm is located rearward in comparison to the first slider arm.

16 Claims, 11 Drawing Sheets

(56) References Cited

U.S. PATENT DOCUMENTS

| | | |
|---|---|---|
| 2004/0097964 A1 | 5/2004 | Dhindsa |
| 2009/0112225 A1 * | 4/2009 | Kaneko ............ A61B 17/32056 |
| | | 606/113 |
| 2012/0116390 A1 * | 5/2012 | Madan ................ H01M 10/425 |
| | | 606/41 |
| 2014/0364868 A1 | 12/2014 | Dhindsa |
| 2016/0074220 A1 | 3/2016 | Ianchulev et al. |
| 2016/0374702 A1 * | 12/2016 | St. George ........... A61B 17/221 |
| | | 606/127 |
| 2018/0028218 A1 | 2/2018 | Pereira et al. |

FOREIGN PATENT DOCUMENTS

| | | | |
|---|---|---|---|
| KR | 20130127424 | 11/2013 | |
| KR | 20200097209 | 8/2020 | |
| WO | WO-2017198673 A1 * | 11/2017 | ............... A61B 1/00 |
| WO | 2020003435 | 1/2020 | |

* cited by examiner

BASKET ACTUATOR AND SURGICAL DEVICE INCLUDING THE SAME

ROSS-REFERENCE TO RELATED APPLICATION(S)

This application claims the benefit of Korean Patent Application No. 10-2020-0106460, filed on Aug. 24, 2020, in the Korean Intellectual Property Office, the disclosure of which is incorporated herein by reference.

BACKGROUND

1. Field of the Invention

One or more example embodiments relate to a basket actuator and a surgical device including the same.

2. Description of the Related Art

A basket is used for endoscopic surgery devices. Once guided into a human body, the basket may open at a desired position, receive an object (e.g., a stone), and close to hold the object. When it is confirmed that the basket is holding the object, a user may take the basket out of the body, thereby removing the object from the body.

In general, the basket may include a plurality of longitudinal members. When the object is small, the object may escape through a space between two neighboring longitudinal members among the plurality of longitudinal members. In this case, an angle of the basket needs to be adjusted. Also, a mechanism for adjusting the angle of the basket may be required for a surgical device.

Since a surgical device including the basket is small in general, there are spatial restrictions on applying an additional mechanism. Accordingly, there is a desire for a technique for adjusting the angle of the basket without excessively increasing the size of the surgical device.

The above description has been possessed or acquired by the inventor(s) in the course of conceiving the present disclosure and is not necessarily an art publicly known before the present application is filed.

SUMMARY

An aspect is to provide a basket actuator and a surgical device including the same.

According to an aspect, there is provided a basket actuator including a base including a base body and a base guide installed in the base body, a slider including a slider body configured to slide along the base guide, and a first slider arm and a second slider arm formed to protrude from the slider body and facing each other, a roller including a roller body rotatably disposed between the first slider arm and the second slider arm and a plurality of roller blades formed to protrude outwardly from the roller body, a wire guide connected to a front end portion of the base body, a wire disposed inside the wire guide and having a first end fixed to the roller, and a basket connected to a second end of the wire, wherein the second slider arm is located rearward in comparison to the first slider arm, and the base further includes a base locking part configured to rotate the roller by interfering with one of the plurality of roller blades while the slider slides backward.

The slider may further include a slider guide formed to protrude from one of the first slider arm and the second slider arm to the other one and configured to rotatably support the roller.

A thickness of the roller may be smaller than a gap between the first slider arm and the second slider arm based on a longitudinal direction of the slider guide.

The roller may be configured to contact the first slider arm while the slider slides backward and contact the second slider arm while the slider slides forward.

The slider may further include a stopper formed to protrude from the second slider arm toward the first slider arm.

The stopper may be spaced apart from the roller when the roller is in contact with the first slider arm and located between the plurality of roller blades when the roller is in contact with the second slider arm.

The base locking part may be configured to rotate the roller while the roller moves backward and passes the base locking part and deformed externally to pass the roller while the roller moves forward and passes the base locking part.

The base locking part may include a locking body formed in parallel with the base body and a locking protrusion formed to inwardly protrude from the locking body.

Among the plurality of roller blades, one roller blade may overlap another roller blade in a direction parallel with a rotation axis of the roller.

The wire and the basket may rotate integrally with the roller.

The basket may be located inside the wire guide at a position in which the roller slides backward and contact the base locking part.

The base may further include an elastic member having one end fixed to the base body and the other end fixed to the slider to contract while the slider moves backward.

According to another aspect, there is also provided a basket actuator including a base including a base body and a base guide installed in the base body, a slider configured to slide along the base guide, a roller including a roller body rotatably connected to the slider and a plurality of roller blades formed to outwardly protrude from the roller body, a wire configured to extend from the roller toward an outside of the base body, and a basket connected to an end portion of the wire, wherein the base further includes a base locking part configured to rotate the roller by interfering with one of the plurality of roller blades while the slider slides backward, and the base locking part is configured to rotate the roller while the roller moves backward and passes the base locking part and deformed externally to pass the roller while the roller moves forward and passes the base locking part.

The slider may include a stopper configured to be spaced apart from the roller while the roller moves backward and passes the base locking part and caught by the roller to prevent the roller from rotating while the roller moves forward and passes the base locking part.

According to another aspect, there is also provided a surgical device including a housing including a housing body and a grip part formed to extend from the housing body and a basket actuator disposed in the housing body, wherein the basket actuator includes a base including a base body and a base guide installed in the base body, a slider including a slider body configured to slide along the base guide, and a first slider arm and a second slider arm formed to protrude from the slider body and facing each other, a roller including a roller body disposed between the first slider arm and the second slider arm to rotate with respect to the slider and a plurality of roller blades formed to outwardly protrude from the roller body, a wire guide connected to a front end portion of the base body, a wire disposed inside the wire guide and having a first end fixed to the roller, and a basket connected to a second end of the wire, wherein the second slider arm is located rearward in comparison to the first slider arm, and the base further includes a base locking part configured to rotate the roller by interfering with one of the plurality of roller blades while the slider slides backward.

The surgical device may further include a trigger connected to the slider, configured to slide along the housing body, and having at least a portion that protrudes outward the housing.

According to example embodiments, it is possible to provide a basket actuator and a surgical device including the same. A user may perform an operation of moving a basket forward and backward, and may selectively perform an operation of expanding or contracting the basket and an operation of changing an angle of the basket only by adjusting a length of a stroke.

Specifically, the user may actuate the basket actuator in a first stroke range and move the basket forward or backward such that the basket is expanded or contracted. Also, the user may actuate the basket actuator in a second stroke range to change the angle of the basket.

According to example embodiments, it is possible to provide a basket actuator and a surgical device including the same with a compact structure.

Additional aspects of example embodiments will be set forth in part in the description which follows and, in part, will be apparent from the description, or may be learned by practice of the disclosure.

BRIEF DESCRIPTION OF THE DRAWINGS

The following drawings attached to this specification exemplarily illustrate some example embodiments of the present disclosure, and serve to facilitate understanding of the technical ideas of the invention with the detailed description, and thus the invention is not limited to the disclosures in the drawings.

DETAILED DESCRIPTION

Figure 1:
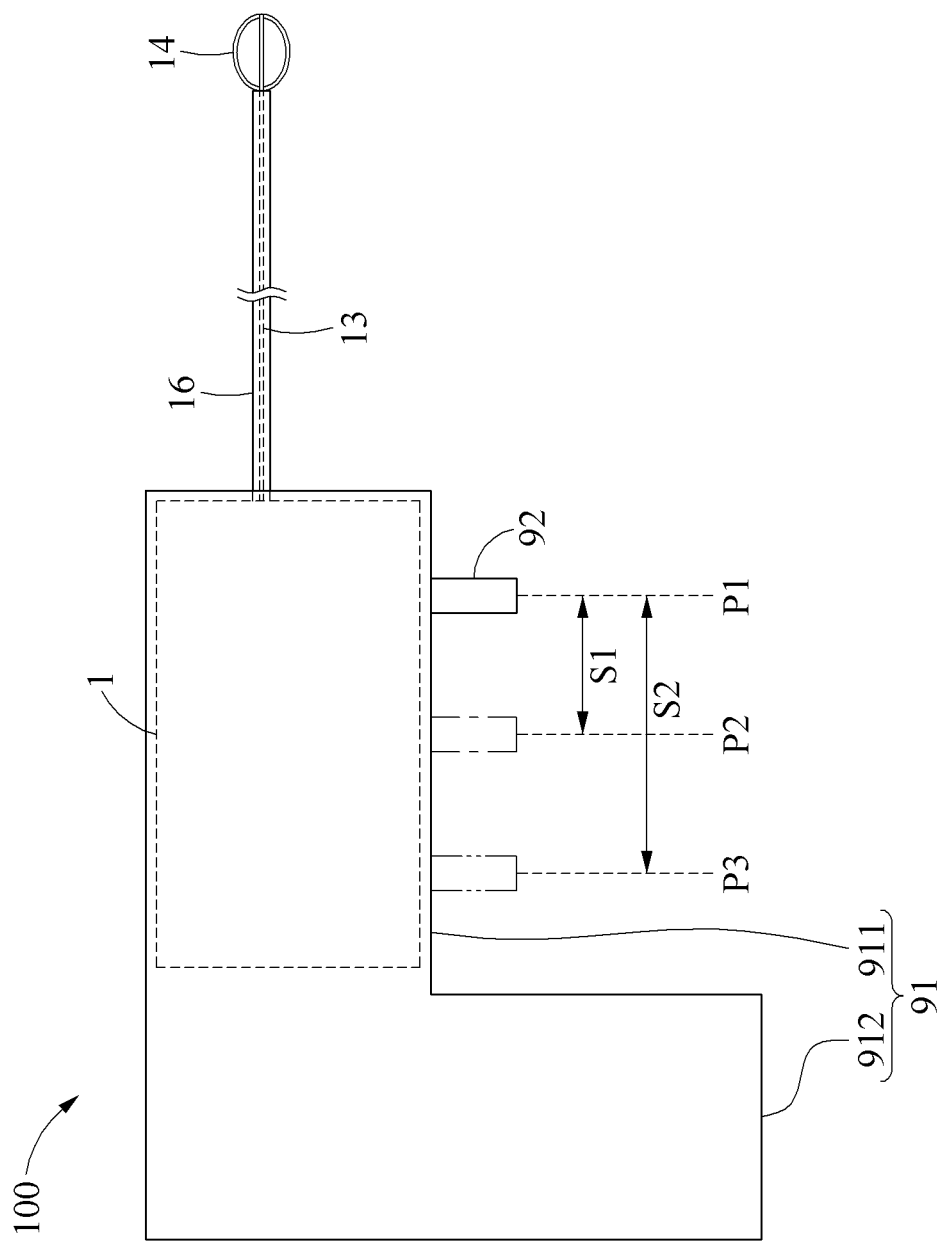
FIG. 1 is a side view illustrating a surgical device according to an example embodiment.

Hereinafter, example embodiments will be described in detail with reference to the accompanying drawings. It should be understood, however, that there is no intent to limit this disclosure to the particular example embodiments disclosed. On the contrary, example embodiments are to cover all modifications, equivalents, and alternatives falling within the scope of the example embodiments.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

A component having a common function with a component included in one example embodiment is described using a like name in another example embodiment. Unless otherwise described, a description made in one example embodiment may be applicable to another example embodiment and a detailed description within a duplicate range is omitted.

FIG. 1 is a side view illustrating a surgical device according to an example embodiment.

Referring to FIG. 1, a surgical device 100 may insert a wire guide into a body of a patient, position a basket at a desired position, and remove a stone using the basket. The surgical device 100 may include a housing 91, a basket actuator 1 included in the housing 91, and a trigger 92 that actuates the basket actuator 1.

The housing 91 may include a housing body 911 including an accommodating space and a grip part 912 formed to extend from the housing body 911. The surgical device 100 may be driven automatically or manually. For example, the surgical device 100 may be driven manually by a user's hand or may be attached to a robot to be driven automatically. As an example, when the surgical device 100 operates manually, a user may operate the surgical device 100 by gripping the grip part 912 with a palm and some fingers and manipulating the trigger 92 with other fingers. As another example, when the surgical device 100 operates automatically, the grip part 912 may be fixed to a robot, and the trigger 92 may be connected to an actuator that realizes a sliding motion. Particularly, when the surgical device 100 is used for a robot surgical device, two operations may be implemented using one actuator without needing to install an actuator for realizing forward and backward movements of a basket 14 separate from an actuator for realizing an angle rotation of the basket 14, which may reduce a weight and cost of the entire surgical device.

The basket actuator 1 may include a wire guide 16 that extends toward an outside of the housing 91, a wire 13 slidably disposed inside the wire guide 16, and the basket 14 connected to an end portion of the wire 13. The basket actuator 1 may adjust an angle or a position of the basket 14 by moving the wire 13 forward or backward or rotating the wire 13. In other words, the angle of the basket 14 may be adjusted by rotating only the wire 13 instead of rotating the housing 91.

The trigger 92 may actuate the basket actuator 1. At least a portion of the trigger 92 may protrude toward the outside of the housing 91. The trigger 92 may move in a range of a first stroke and move in a range of a second stroke. Here, the first stroke S1 may be a range formed between a first position P1 (refer to FIG. 2) and a second position P2 (refer to FIG. 6). The second stroke S2 may be a range formed between the first position P1 and a third position P3 (refer to FIG. 8). The first position through the third position will be described in detail later.

When the trigger 92 moves in the range of the first stroke S1, the basket 14 may move forward or backward without an angular change. When the trigger 92 moves in the range of the second stroke S2, the basket 14 may move forward or backward and change in angle.

Figure 2:
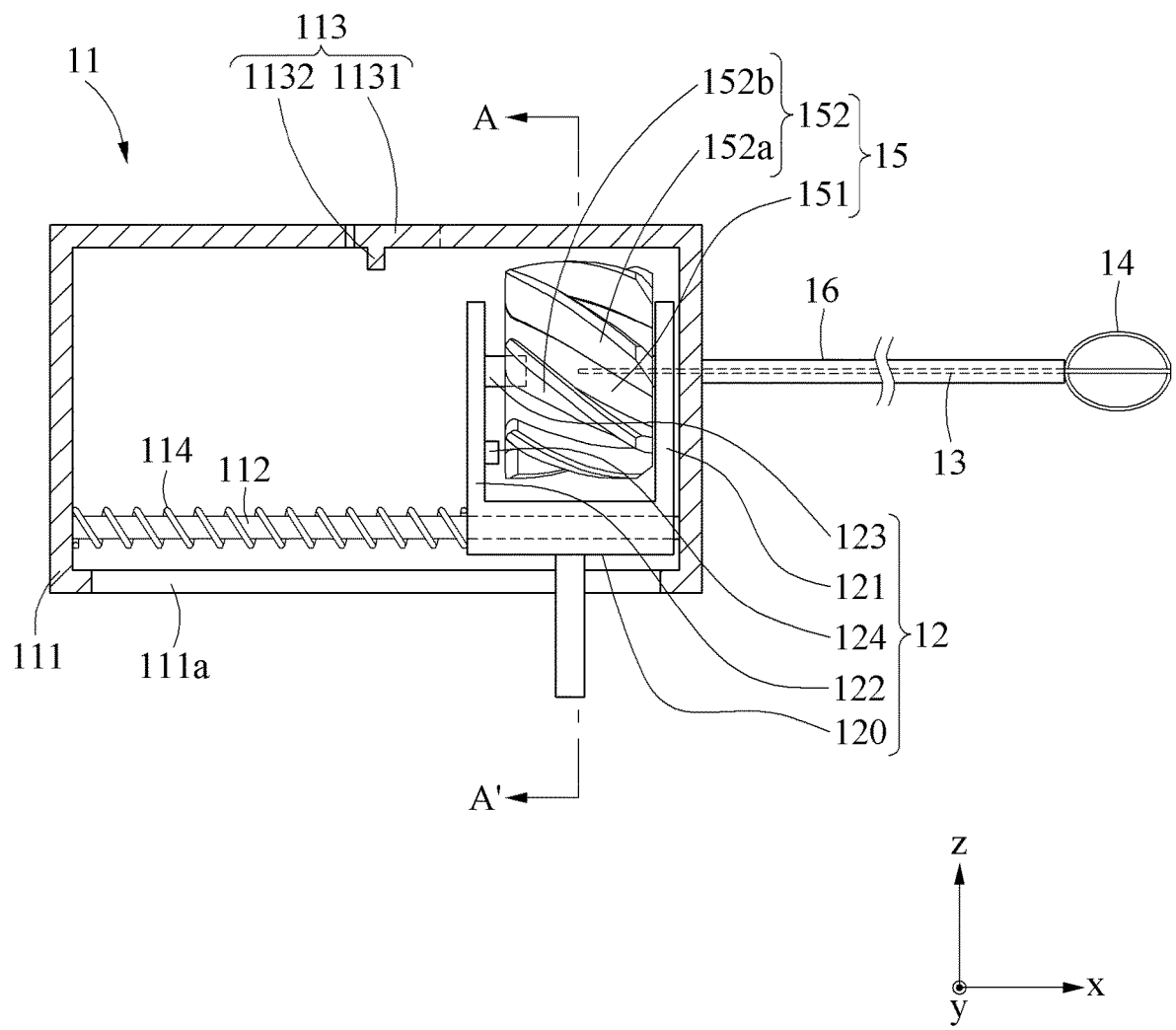
FIG. 2 is a longitudinal sectional view illustrating a basket actuator according to an example embodiment.
Figure 3:
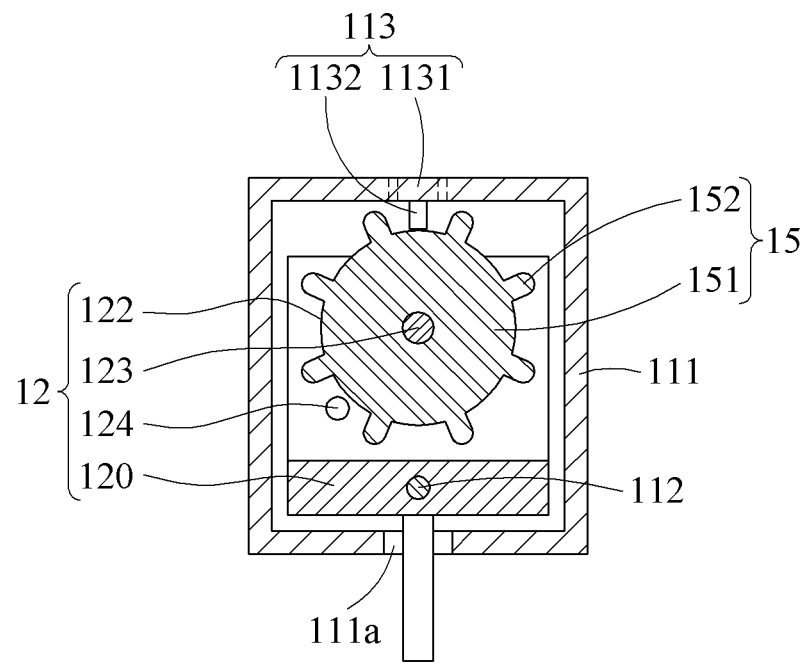
FIG. 3 is a transverse sectional view illustrating a basket actuator according to an example embodiment.
Figure 4:
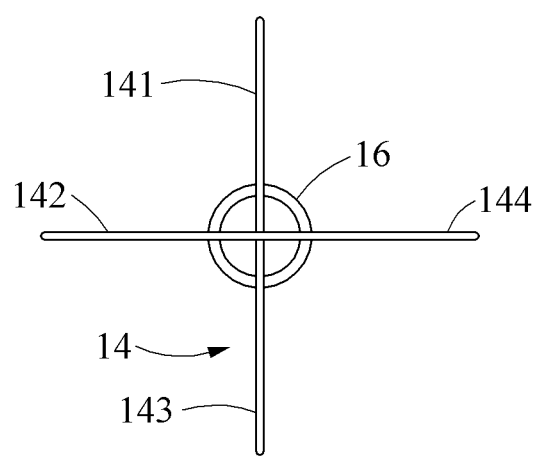
FIG. 4 is a front view illustrating a basket and a wire guide in a state of FIG. 2.

FIG. 2 is a longitudinal sectional view illustrating a basket actuator according to an example embodiment and FIG. 3 is a transverse sectional view illustrating a basket actuator according to an example embodiment. FIG. 4 is a front view illustrating a basket and a wire guide in a state of FIG. 2.

Referring to FIGS. 2 through 4, a basket actuator may include a base 11, a slider 12, the wire 13, the basket 14, a roller 15, and the wire guide 16. In FIG. 2, a position at which the slider 12 is located may be referred to as a "first position." At the first position, the slider 12 may be in contact with a front inner wall of the base 11.

The base 11 may include a base body 111, a base guide 112 installed in the base body 111, a base locking part 113 connected to one side wall of the base body 111, and an elastic member 114.

The base body 111 may have an accommodating space therein. The base guide 112 may be a shaft that connects a front inner wall and a rear inner wall of the base body 111. The base guide 112 may guide the sliding of the slider 12. The base locking part 113 may interfere with the roller 15 to rotate the roller 15. The base locking part 113 may include a locking body 1131 formed in parallel with a side wall of the base body 111 and a locking protrusion 1132 formed to inwardly protrude from the locking body 1131. The elastic member 114 may apply an elastic force to the slider 12 to assist the slider 12 with remaining at an initial position (the first position) unless an external force is applied.

The slider 12 may include a slider body 120 configured to slide along the base guide 112, a first slider arm 121 and a second slider arm 122 formed to protrude from the slider body 120 and facing each other, a slider guide 123 formed to protrude from one of the first slider arm 121 and the second slider arm 122 toward the other one and configured to rotatably support the roller 15, and a stopper 124 formed in the second slider arm 122 and disposed to be spaced apart from the slider guide 123.

The slider body 120 may reciprocate with one degree of freedom along the base guide 112. The slider body 120 may be connected to a trigger. The trigger may move along a slot 111a formed in the base body 111. A user may apply a force to the trigger to move the slider 12.

The first slider arm 121 and the second slider arm 122 may have a shape of a plate. A distance between the first slider arm 121 and the second slider arm 122 may be greater than a height of the roller 15. In the above structure, depending on a moving direction of the slider 12, the roller 15 may slide in a state of being supported by the first slider arm 121 (that is, a state of being spaced apart from the second slider arm 122), or slide in a state opposite thereto. For example, at the first position, the first slider arm 121 may be in contact with the front inner wall of the base body 111. The second slider arm 122 may be located rearward in comparison to the first slider arm 121.

The slider guide 123 may be inserted into a central portion of the roller 15 to serve as a rotation axis of the roller 15.

The stopper 124 may be formed to protrude from the second slider arm 122 toward the first slider arm 121. The stopper 124 may be spaced apart from the roller 15 when the roller 15 is in contact with the first slider arm 121, and interfere with the roller 15 to prevent the roller 15 from rotating when the roller 15 is in contact with the second slider arm 122.

The wire 13 may have one end connected to the roller 15 and the other end connected to the basket 14. The wire 13 may be provided in the wire guide 16 and pass the first slider arm 121.

The basket 14 may be connected to the wire 13. The basket 14 may open when exposed to an outside of the wire guide 16. Also, when the basket 14 is moved backwardly (in a −x direction) by the wire 13 and inserted into the wire guide 16, the basket 14 may close.

The roller 15 may include a roller body 151 rotatably disposed between the first slider arm 121 and the second slider arm 122 and a plurality of roller blades 152 formed to outwardly protrude from the roller body 151. The plurality of roller blades 152 may be spirally formed along an outer surface of the roller body 151. Based on a longitudinal direction of the slider guide 123, a thickness of the roller 15 may be smaller than a gap between the first slider arm 121 and the second slider arm 122.

The plurality of roller blades 152 may overlap each other based on a direction (e.g., an x-axial direction) parallel with a rotation axis of the roller 15. For example, the plurality of roller blades 152 may include a first roller blade 152a and a second roller blade 152b neighboring each other. A front end portion of the first roller blade 152a may overlap a rear end portion of the second roller blade 152a based on a direction parallel with the rotation axis of the roller 15. In the above structure, a phenomenon that the base locking part 113 passes the roller 15 without interfering with any one of the plurality of roller blades 152 may be prevented.

The base locking part 113 may rotate the roller 15 by interfering with one of the plurality of roller blades 152 while the slider 12 slides backward. Since the wire 13 and the basket 14 rotates integrally with the roller 15, when the roller 15 rotates, the wire 13 and the basket 14 may rotate together so that an angle of the basket 14 is changed.

The wire guide 16 may be connected to the front end portion of the base body 111. The wire guide 16 may communicate with an internal space of the base body 111. The wire guide 16 may be deformable.

Referring to FIG. 4, the basket 14 may include a plurality of longitudinal members 141, 142, 143, and 144. Although the drawings illustrate four longitudinal members, the number of longitudinal members is not limited thereto.

Figure 5:
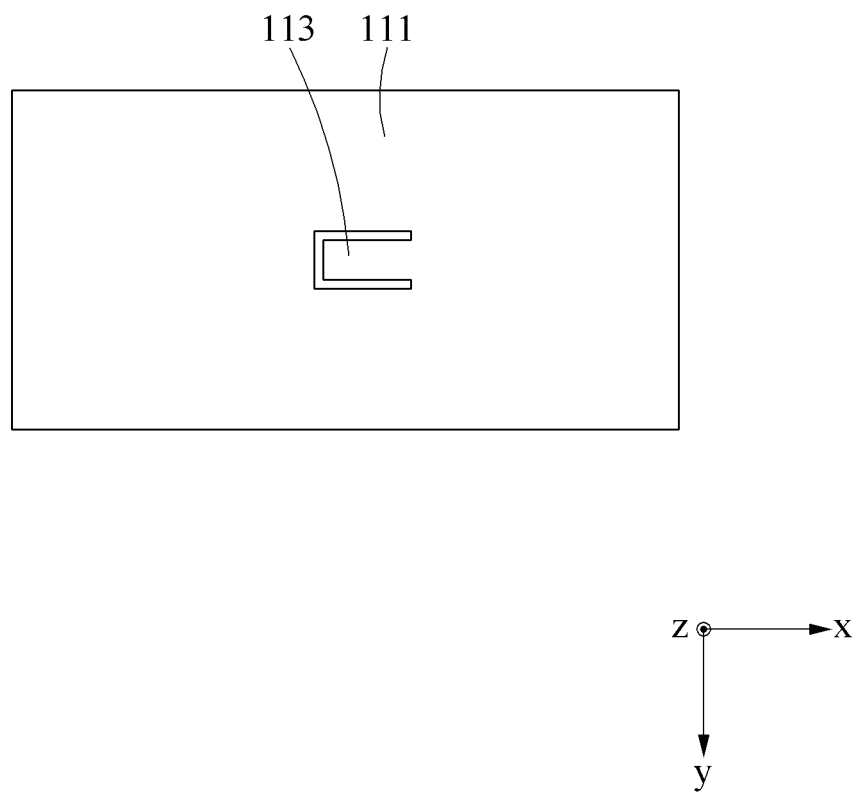
FIG. 5 is a side view illustrating a base according to an example embodiment.

FIG. 5 is a side view illustrating a base according to an example embodiment.

Referring to FIG. 5, the base locking part 113 may be connected to the base body 111 and partially separated so as to move relative to the base body 111. For example, the base locking part 113 may have three portions spaced apart from the base body 111 at preset intervals. In this example, only one of the three portions may be connected to the base body 111. In other words, the base locking part 113 may have a cantilever shape. When an external force is applied to the base locking part 113, since the base locking part 113 includes a locking protrusion (not shown) formed to protrude toward an inside (in a −z direction) of the base body 111, the base locking part 113 may be deformed toward the outside (in a +z direction) of the base body 111 in response to the external force being applied to the locking protrusion.

Although the above description and drawings are based on a case in which the base locking part 113 is provided in one side wall (e.g., +z-directional side surface) of the base body 111, it is merely an example. For example, the base locking part 113 may be additionally formed in a −y-directional side surface of the base body 111.

Figure 6:
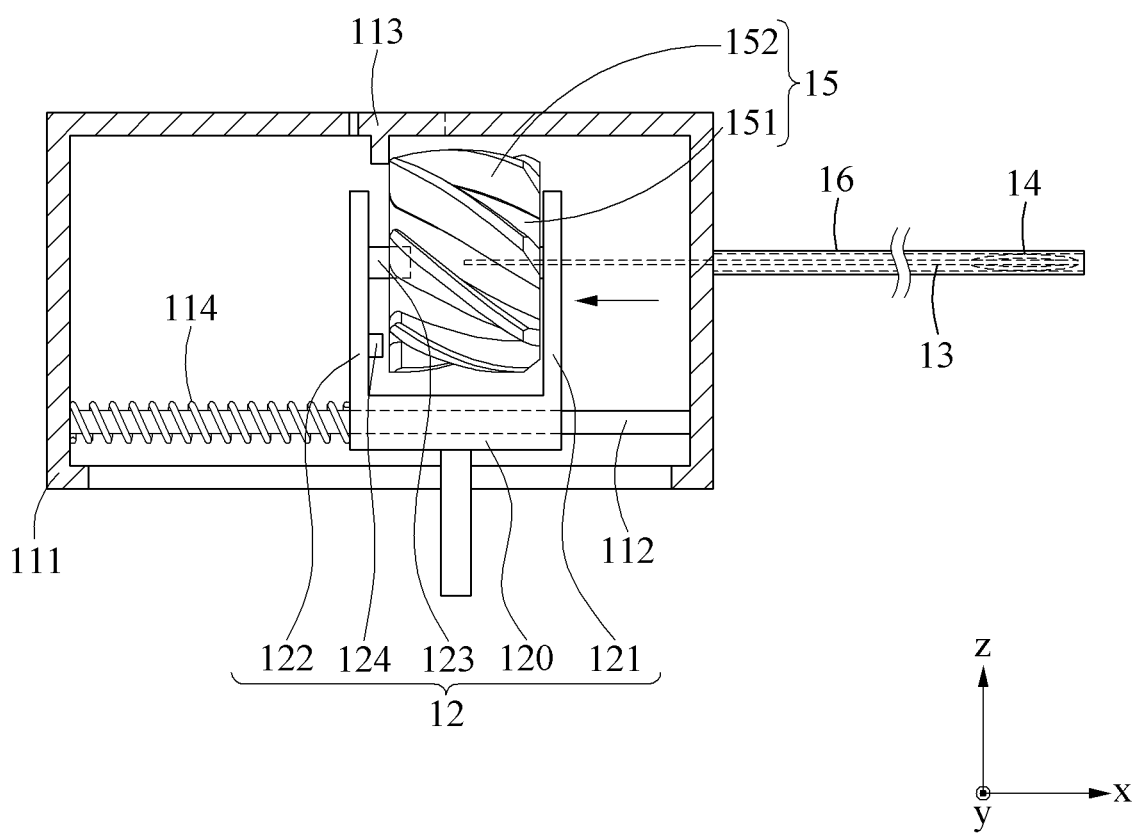
FIG. 6 is a longitudinal sectional view illustrating a basket actuator according to an example embodiment in a state in which a slider 12 slides backwardly (in a −x direction) when compared to FIG. 2.
Figure 7:
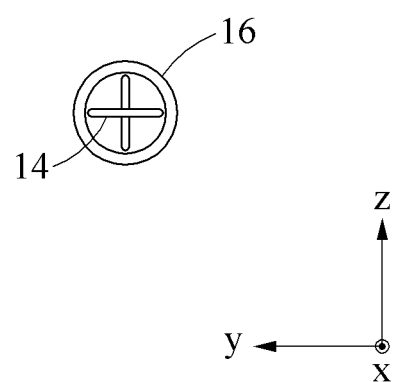
FIG. 7 is a front view illustrating a basket and a wire guide in a state of FIG. 6.

FIG. 6 is a longitudinal sectional view illustrating a basket actuator according to an example embodiment in a state in which a slider 12 slides backwardly (in a −x direction) when compared to FIG. 2. FIG. 7 is a front view illustrating a basket and a wire guide in a state of FIG. 6.

Figure 8:
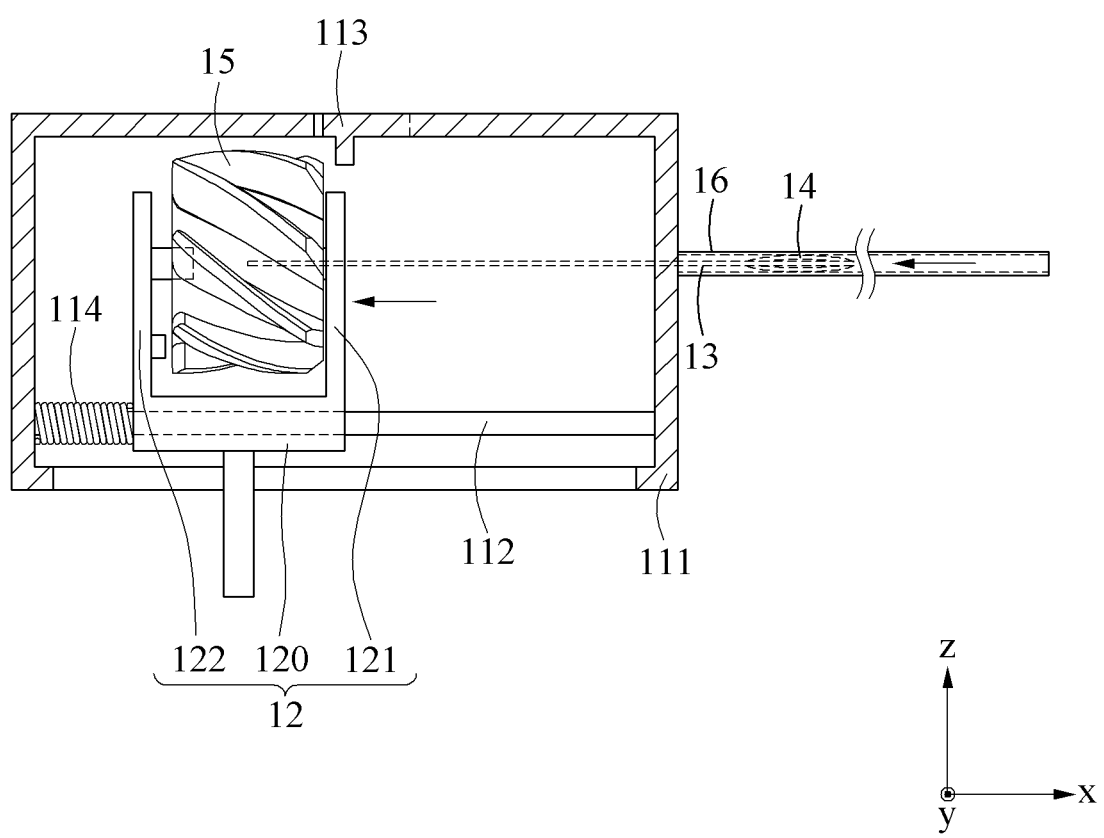
FIG. 8 is a longitudinal sectional view illustrating a basket actuator according to an example embodiment in a state in which the slider 12 slides much backwardly (in a −x direction) when compared to FIG. 6.
Figure 9:
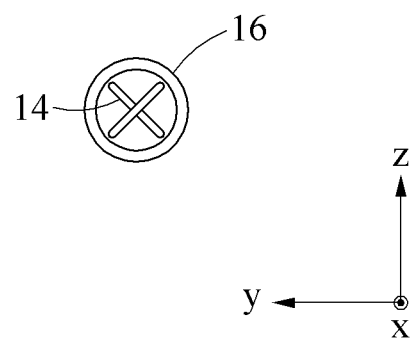
FIG. 9 is a front view illustrating a basket and a wire guide in a state of FIG. 8.

FIG. 8 is a longitudinal sectional view illustrating a basket actuator according to an example embodiment in a state in which the slider 12 slides much backwardly (in a −x direction) when compared to FIG. 6. FIG. 9 is a front view illustrating a basket and a wire guide in a state of FIG. 8.

In FIG. 6, a position of the slider 12 is referred to as a "second position." As the second position, the roller 15 may be in contact with the base locking part 113. In FIG. 8, a position of the slider 12 is referred to as a "third position." At the third position, the roller 15 has completely passed the base locking part 113.

Referring to FIGS. 6 through 9, while the slider 12 moves backward, the roller 15 may contact the base locking part 113. While the slider 12 moves backward, the roller body 151 may contact the first slider arm 121 and the stopper 124 may be spaced apart from the roller blades 152. Since the stopper 124 is spaced apart from the roller blades 152, the roller 15 may be able to rotate based on the slider guide 123. The base locking part 113 may contact one of the plurality of roller blades 152 to rotate the roller 15. The slider body 120 may press the elastic member 114 to contract the elastic member 114.

While the slider 12 moves from a first position to the second position, the basket 14 may be moved backward by the wire 13 and move into the wire guide 16.

When the slider 12 is moved between the first position and the second position, in other words, when the slider 12 is driven in a range of the first stroke S1 (refer to FIG. 1), the rotation of the roller 15 may be prevented by the base locking part 113. Thus, the basket 14 may be moved forward or backward while the angle of the basket 14 is maintained.

When the slider 12 is moved between the first position and the third position, in other words, when the slider 12 is driven in a range of the second stroke S2 (refer to FIG. 1), the roller 15 may be rotated by the base locking part 113, so that the angle of the basket 14 may be changed.

Figure 10:
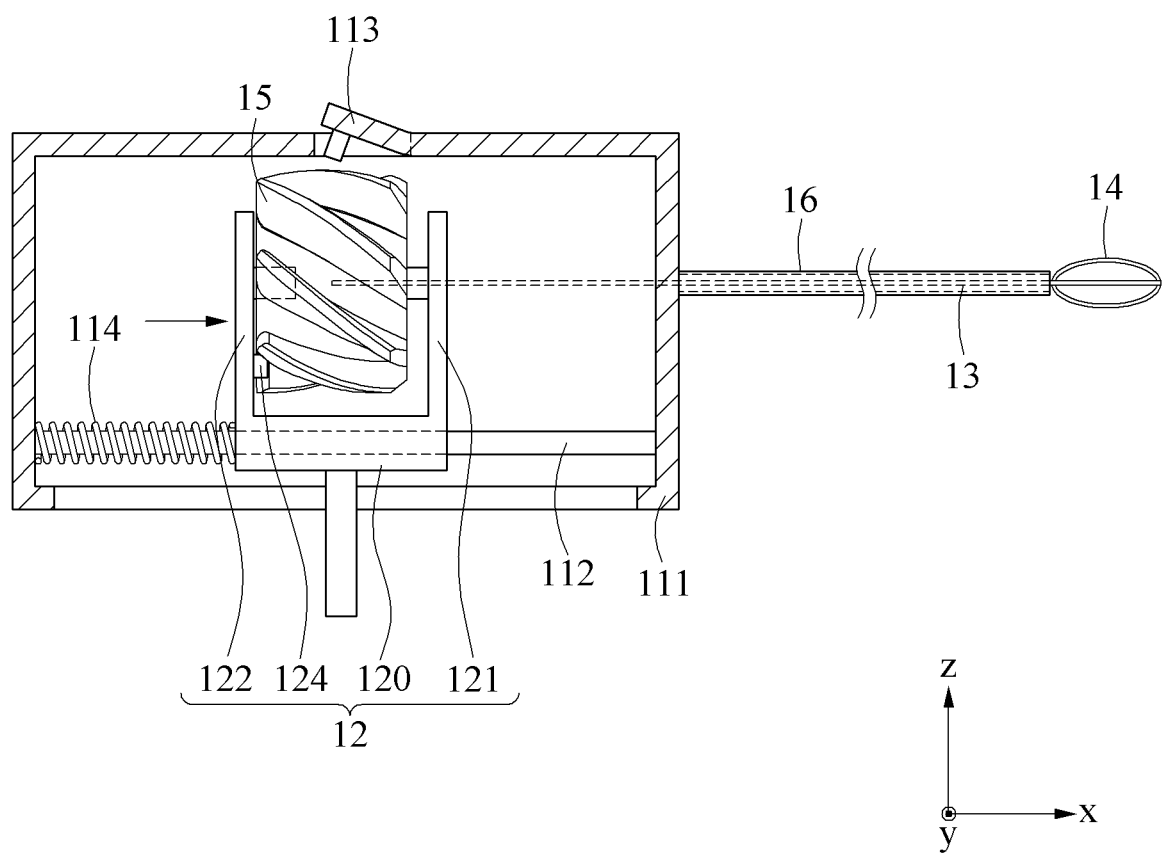
FIG. 10 is a longitudinal sectional view illustrating a basket actuator according to an example embodiment in a state in which the slider 12 slides forwardly (in a +x direction) when compared to FIG. 8.
Figure 11:
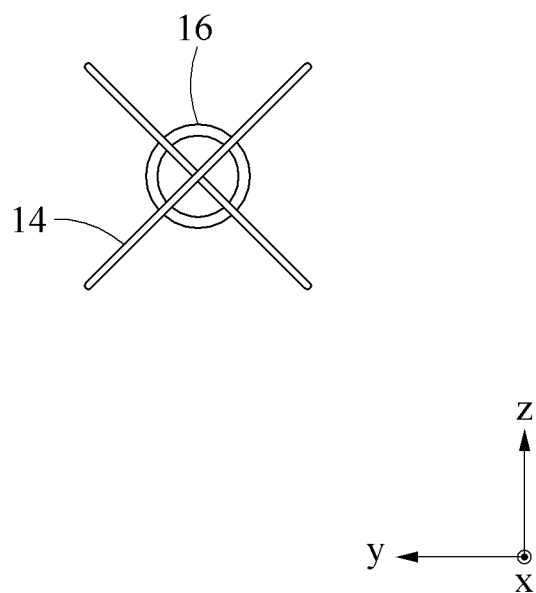
FIG. 11 is a front view illustrating a basket and a wire guide in a state of FIG. 10.

FIG. 10 is a longitudinal sectional view illustrating a basket actuator according to an example embodiment in a state in which the slider 12 slides forwardly (in a +x direction) when compared to FIG. 8. FIG. 11 is a front view illustrating a basket and a wire guide in a state of FIG. 10.

Referring to FIGS. 10 and 11, while the slider 12 moves forward, the roller 15 may contact the base locking part 113. While the slider 12 moves forward, the roller body 151 may contact the second slider arm 122, and the stopper 124 may be caught by one of the plurality of roller blades 152. Since the stopper 124 is caught by one of the plurality of roller blades 152, the roller 15 may be unable to rotate based on the slider guide 123. The slider body 120 may move forward by a restoring force of the elastic member 114.

While the slider 12 returns to the first position, the rotation of the roller 15 may be blocked, and the base locking part 113 may be deformed externally.

While this disclosure includes specific example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example embodiment are to be considered as being applicable to similar features or aspects in other example embodiments. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A basket actuator comprising:
    a base comprising a base body and a base guide installed in the base body;
    a slider comprising a slider body configured to slide along the base guide, and a first slider arm and a second slider arm formed to protrude from the slider body and facing each other;
    a roller comprising a roller body rotatably disposed between the first slider arm and the second slider arm and a plurality of roller blades formed to protrude outwardly from the roller body;
    a wire guide connected to a front end portion of the base body;
    a wire disposed inside the wire guide and having a first end fixed to the roller; and
    a basket connected to a second end of the wire,
    wherein the second slider arm is located rearward in comparison to the first slider arm, and
    the base further comprises a base locking part configured to rotate the roller by interfering with one of the plurality of roller blades while the slider slides backward.

2. The basket actuator of claim 1, wherein the slider further comprises a slider guide formed to protrude from one of the first slider arm and the second slider arm to the other one and configured to rotatably support the roller.

3. The basket actuator of claim 2, wherein a thickness of the roller is smaller than a gap between the first slider arm and the second slider arm based on a longitudinal direction of the slider guide.

4. The basket actuator of claim 1, wherein the roller is configured to contact the first slider arm while the slider slides backward and contact the second slider arm while the slider slides forward.

5. The basket actuator of claim 4, wherein the slider further comprises a stopper formed to protrude from the second slider arm toward the first slider arm.

6. The basket actuator of claim 5, wherein the stopper is spaced apart from the roller when the roller is in contact with the first slider arm and located between the plurality of roller blades when the roller is in contact with the second slider arm.

7. The basket actuator of claim 1, wherein the base locking part is configured to rotate the roller while the roller moves backward and passes the base locking part and configured to be deformed externally to pass the roller while the roller moves forward and passes the base locking part.

8. The basket actuator of claim 1, wherein the base locking part comprises:
a locking body formed in parallel with the base body; and
a locking protrusion formed to inwardly protrude from the locking body.

9. The basket actuator of claim 1, wherein, among the plurality of roller blades, one roller blade overlaps another roller blade in a direction parallel with a rotation axis of the roller.

10. The basket actuator of claim 1, wherein the wire and the basket rotate integrally with the roller.

11. The basket actuator of claim 1, wherein the basket is located inside the wire guide at a position in which the roller slides backward and contacts the base locking part.

12. The basket actuator of claim 1, wherein the base further comprises an elastic member having a first end fixed to the base body and a second end fixed to the slider to contract while the slider moves backward.

13. A basket actuator comprising:
a base comprising a base body and a base guide installed in the base body;
a slider configured to slide along the base guide;
a roller comprising a roller body rotatably connected to the slider and a plurality of roller blades formed to outwardly protrude from the roller body;
a wire configured to extend from the roller toward an outside of the base body; and
a basket connected to an end portion of the wire;
wherein the base further comprises a base locking part configured to rotate the roller by interfering with one of the plurality of roller blades while the slider slides backward, and
the base locking part is configured to rotate the roller while the roller moves backward and passes the base locking part and configured to be deformed externally to pass the roller while the roller moves forward and passes the base locking part.

14. The basket actuator of claim 13, wherein the slider comprises a stopper configured to be spaced apart from the roller while the roller moves backward and passes the base locking part and configured to be caught by the roller to prevent the roller from rotating while the roller moves forward and passes the base locking part.

15. A surgical device comprising:
a housing comprising a housing body and a grip part formed to extend from the housing body; and
a basket actuator disposed in the housing body,
wherein the basket actuator comprises:
a base comprising a base body and a base guide installed in the base body;
a slider comprising a slider body configured to slide along the base guide, and a first slider arm and a second slider arm formed to protrude from the slider body and facing each other;
a roller comprising a roller body disposed between the first slider arm and the second slider arm to rotate with respect to the slider and a plurality of roller blades formed to outwardly protrude from the roller body;
a wire guide connected to a front end portion of the base body;
a wire disposed inside the wire guide and having a first end fixed to the roller; and
a basket connected to a second end of the wire,
wherein the second slider arm is located rearward in comparison to the first slider arm, and
the base further comprises a base locking part configured to rotate the roller by interfering with one of the plurality of roller blades while the slider slides backward.

16. The surgical device of claim 15, further comprising:
a trigger connected to the slider, configured to slide along the housing body, and having at least a portion that protrudes outwardly from the housing.

* * * * *